United States Patent
Auvray et al.

(10) Patent No.: US 11,207,042 B2
(45) Date of Patent: Dec. 28, 2021

(54) VASCULAR TREATMENT OUTCOME VISUALIZATION

(75) Inventors: Vincent Maurice Andre Auvray, Meudon (FR); Raoul Florent, Ville d'Avray (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 103 days.

(21) Appl. No.: 14/240,853

(22) PCT Filed: Aug. 24, 2012

(86) PCT No.: PCT/IB2012/054294
§ 371 (c)(1),
(2), (4) Date: Feb. 25, 2014

(87) PCT Pub. No.: WO2013/035005
PCT Pub. Date: Mar. 14, 2013

(65) Prior Publication Data
US 2014/0204124 A1  Jul. 24, 2014

Related U.S. Application Data

(60) Provisional application No. 61/531,144, filed on Sep. 6, 2011.

(51) Int. Cl.
*G06T 7/00* (2017.01)
*G06T 3/00* (2006.01)
(Continued)

(52) U.S. Cl.
CPC ................ *A61B 6/504* (2013.01); *A61B 6/12* (2013.01); *A61B 6/463* (2013.01); *A61B 6/503* (2013.01);
(Continued)

(58) Field of Classification Search
None
See application file for complete search history.

(56) References Cited

U.S. PATENT DOCUMENTS 5,077,769 A  12/1991  Franciose
5,285,786 A   2/1994  Fujii
(Continued)

FOREIGN PATENT DOCUMENTS

EP    0463533 A1   1/1992
JP  2009101208 A   5/2009
(Continued)

OTHER PUBLICATIONS

Egger, Jan et al "A Software System for Stent Planning, Stent Simulation and Follow-Up Examinations in the Vascular Domain", IEEE, 2009.
(Continued)

*Primary Examiner* — Phuc N Doan

(57) ABSTRACT

The present invention relates to vascular treatment outcome visualization. To provide an enhanced possibility to check that a vascular treatment has been correctly performed, it is proposed to provide (112) a first image data (114) of a region of interest of a vascular structure at a first point in time, and to provide (116) at least one second image data (118) of the region of interest of the vascular structure at a second point in time, wherein a vascular treatment has been applied to the vascular structure between the first point in time and the second point in time. Further, the first and the at least one second image data are combined (120) generating a joint outcome visualization image data (122) and the joint outcome visualization image data is displayed (124).

20 Claims, 11 Drawing Sheets

(51) Int. Cl.
  *G06T 11/60* (2006.01)
  *A61B 6/00* (2006.01)
  *A61B 6/12* (2006.01)
  *A61B 6/03* (2006.01)
  *A61B 5/00* (2006.01)
  *A61B 5/055* (2006.01)

(52) U.S. Cl.
  CPC .......... *A61B 6/5235* (2013.01); *G06T 3/0068* (2013.01); *G06T 7/0016* (2013.01); *G06T 11/60* (2013.01); *A61B 5/0044* (2013.01); *A61B 5/055* (2013.01); *A61B 6/032* (2013.01); *A61B 6/469* (2013.01); *A61B 6/481* (2013.01); *A61B 6/487* (2013.01); *A61B 6/5264* (2013.01); *A61B 6/5288* (2013.01); *G06T 2207/10081* (2013.01); *G06T 2207/20221* (2013.01); *G06T 2207/30101* (2013.01)

(56) References Cited

U.S. PATENT DOCUMENTS

| | | | |
|---|---|---|---|
| 6,370,417 B1 | 4/2002 | Horbaschek et al. | |
| 7,650,179 B2 | 1/2010 | Redel | |
| 8,781,257 B2 * | 7/2014 | Bruijns | G06T 7/30 382/294 |
| 2003/0220555 A1 | 11/2003 | Heigl et al. | |
| 2004/0170685 A1 | 9/2004 | Carpenter | |
| 2004/0210214 A1 * | 10/2004 | Knowlton | A61B 18/14 606/41 |
| 2005/0027187 A1 * | 2/2005 | Barth | G06F 19/00 600/407 |
| 2007/0276216 A1 | 11/2007 | Beyar | |
| 2008/0009715 A1 | 1/2008 | KUKUK et al | |
| 2008/0051657 A1 | 2/2008 | Rold | |
| 2008/0199097 A1 | 8/2008 | Mory | |
| 2008/0279476 A1 | 11/2008 | Rongen et al. | |
| 2009/0203962 A1 | 8/2009 | Miller | |
| 2009/0216112 A1 | 8/2009 | Assis | |
| 2010/0061603 A1 | 3/2010 | Mielekamp | |
| 2010/0061611 A1 * | 3/2010 | Xu | G06T 7/136 382/131 |
| 2010/0125282 A1 * | 5/2010 | Machek | A61B 34/30 606/130 |
| 2010/0160764 A1 * | 6/2010 | Steinberg | G06T 7/13 600/407 |
| 2010/0208973 A1 | 8/2010 | Leinard et al. | |
| 2010/0240986 A1 * | 9/2010 | Stiles | 600/424 |
| 2011/0026786 A1 * | 2/2011 | Mohamed | G06F 19/321 382/128 |
| 2011/0033088 A1 | 2/2011 | Rekimoto | |
| 2011/0201915 A1 | 8/2011 | Gogin et al. | |

FOREIGN PATENT DOCUMENTS

| | | |
|---|---|---|
| JP | 2010240255 A | 10/2010 |
| WO | WO2011039673 | 4/2011 |

OTHER PUBLICATIONS

Egger, Jan et al "Aorta Segmentation for Stent Simulation", C12BM09—Miccai Workshop on Cardiovascular Interventional Imaging and Biophysical Modelling, 2009.

Blasel, Stella et al "Recanalization Results after Intracranial Stenting of Atherosclerotic Stenoses" Cardiovascular and Interventional Radiology, vol. 33, No. 5, 2010, pp. 914-920.

* cited by examiner

VASCULAR TREATMENT OUTCOME VISUALIZATION

CROSS-REFERENCE TO PRIOR APPLICATIONS

This application is the U.S. National Phase application under 35 U.S.C. § 371 of International Application Serial No. PCT/IB2012/054294, filed on Aug. 24, 2012, which claims the benefit of U.S. Application Ser. No. 61/531,144, filed on Sep. 6, 2011. These applications are hereby incorporated by reference herein.

FIELD OF THE INVENTION

The present invention relates to vascular treatment outcome visualization. The present invention relates in particular to a device for vascular treatment outcome visualization, a medical imaging system for vascular treatment outcome visualization, a method for vascular treatment outcome visualization, as well as a computer program element and a computer readable medium.

BACKGROUND OF THE INVENTION

In vascular treatments, for example in percutaneous coronary intervention, for example treating cardiac stenosis, it is of importance to control a correct performance of the treatment. One possibility can be seen in acquiring images of the region of interest after the vascular treatment and to have these images inspected by the surgeon, for example. U.S. Pat. No. 7,941,000 describes providing a view on a post-deployment situation. However, it has been shown that this allows only assessing the final situation. An evaluation in the sense of whether an appropriate treatment has occurred is not possible.

SUMMARY OF THE INVENTION

There is a need to provide an enhanced possibility to check that a vascular treatment has been correctly performed.

The object of the present invention is solved by the subject-matter of the independent claims, wherein further embodiments are incorporated in the dependent claims.

It should be noted that the following described aspects of the invention apply also for the device for vascular treatment outcome visualization, the medical imaging system for vascular treatment outcome visualization, the method for vascular treatment outcome visualization, as well as for the computer program element and the computer readable medium.

According to a first aspect of the present invention, a device for vascular treatment outcome visualization is provided, that comprises a processing unit, an interface unit and a display unit. The interface unit is configured to provide the processing unit with a first image data of a region of interest of a vascular structure at a first point in time, and to provide the processing unit with at least one second image data of a region of interest of a vascular structure at a second point in time; wherein, between the first point in time and the second point in time, a vascular treatment is provided to be applied to the vascular structure. The processing unit is configured to combine the first and the at least one second image data to generate a joint outcome visualization image data. The display unit is configured to display the joint outcome visualization image data.

According to an exemplary embodiment of the invention, the processing unit is configured to register the first and the second image data for the combination.

According to an exemplary embodiment of the invention, the vascular treatment comprises a placement of a predetermined medical device inside a vascular structure. The interface unit is configured to provide a device image data of the placed device. The processing unit is configured to combine the device image data, in addition to the first image data and the second image data, to generate the joint outcome visualisation image data.

According to an exemplary embodiment of the invention, the processing unit is configured to register the device image data with at least the first or/and the second image data.

According to an exemplary embodiment of the invention, for the second image data, the interface unit is configured to provide a plurality of images of a first subset of images, in which the device is visible, and to provide at least one image of a second subset of images as a mask image data, in which the vascular structure is visible. The first subset of images and the second subset of images relate to a point in time after the vascular treatment has been applied. The processing unit is configured to register and combine the plurality of images of the first subset of images to each other along time to generate a boosted device image data in which regions relating to the device are boosted. The processing unit is configured to combine the first image data, the boosted device image data, and the mask image data to generate the joint outcome visualization image data.

The combination of the plurality of images may comprise an averaging of the plurality of images.

According to a second aspect of the present invention, a medical imaging system for vascular treatment outcome visualization is provided, that comprises an image acquisition unit and a device for vascular treatment outcome visualization according to one of the above mentioned embodiments. The image acquisition unit is configured to provide the first image data of the region of interest of the vascular structure at a point in time and to provide the second image data of the region of interest of the vascular structure at the second point in time.

According to a third aspect of the present invention, a method for vascular treatment outcome visualization is provided, comprising the following steps:
a) providing a first image data of a region of interest of a vascular structure at a first point in time;
b) providing at least one second image data of the region of interest of the vascular structure at a second point in time;
c) combining the first and the at least one second image data generating a joint outcome visualization image data; and
d) displaying the joint outcome visualization image data.

According to an exemplary embodiment of the invention, the vascular treatment comprises placing a predetermined medical device inside the vascular structure. In addition to the first image data and the second image data, a device image data of the placed device is also combined to generate the joint outcome visualization image data.

For the combination, the device image data may be registered with at least the first or/and the second image data.

According to an exemplary embodiment of a method of the invention, a plurality of images of the first subset of images, in which the device is visible, are registered to each other along time generating a boosted device image data in which regions relating to the device are boosted. At least one image of a second subset of images is provided as a mask image data, in which the vascular structure is visible. The first subset of images and the second subset of images relate to a point in time after the vascular treatment has been applied. In step c), the first image data, the boosted device image data and the mask image data are combined to generate the joint outcome visualization image data.

According to an aspect of the present invention, it is proposed to build a synthetic visualization of the vascular treatment, which treatment for example can comprise a stenting operation. An image is generated showing the lumen before and after the vascular treatment, for example before and after stenting. Thus, a clinician can easily check that the operation was correctly performed. Further, also the procedure is documented in a single synthetic image, i.e. the joint outcome visualization image, which is easily understandable by both the clinician and the patient himself.

It is an aspect of the present invention to generate an image of a summary, so-to-speak, so that the clinician, as well as the patient, can see how the vessel was treated, for example opened by stenting. Further, in case of stenting, it is also possible to superimpose the stent in form of a stent boost image, for example, to see if the stent rests to the vessel's wall as intended. The resulting image is a new type of summary image, in which it is possible to see if an intervention that has been taken place was a success or not. The joint outcome visualization image also serves as a documentation of the process, since the pre-treatment state, as well as the post-treatment state, are shown in one image.

These and other aspects of the invention will become apparent from and elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
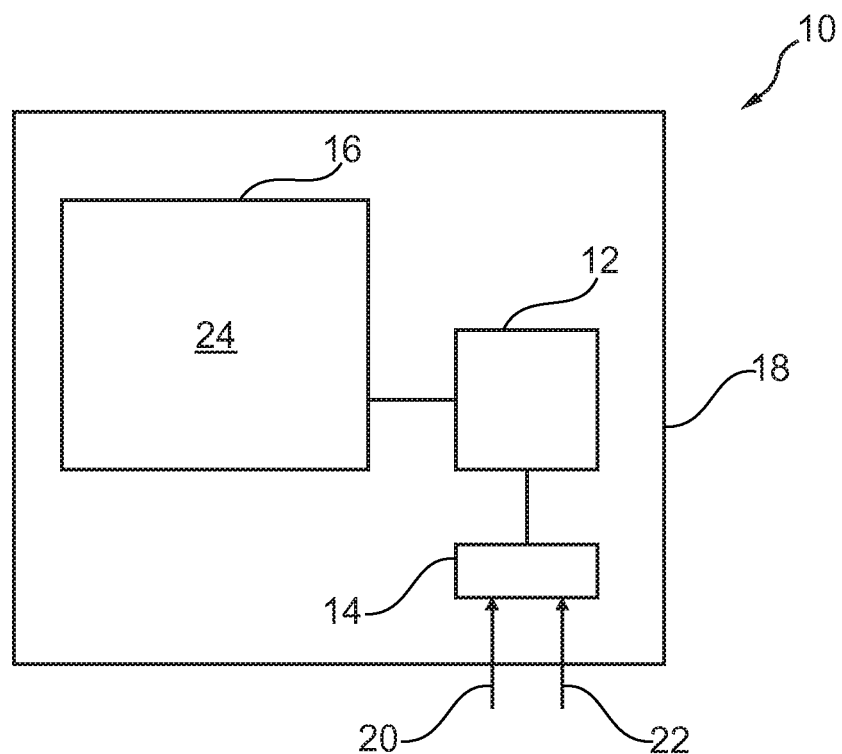
FIG. 1 shows an exemplary embodiment of a device for vascular treatment outcome visualization according to the present invention.

FIG. 1 shows a device 10 for vascular treatment outcome visualization, comprising a processing unit 12, an interface unit 14, and a display unit 16.

An enclosing frame 18 indicates the possibility to arrange the processing unit 12, the interface unit 14, and the display unit 16 inside a common housing. However, it must be noted that the respective units can also be provided as separate components connected to each other to form the device 10.

The interface unit 14 is configured to provide the processing unit with a first image data of a region of interest of a vascular structure at a first point in time. For example, the first image data provision is indicated with a first entering arrow 20. The interface unit 14 is further configured to provide the processing unit 12 with at least one second image data of a region of interest of a vascular structure at a second point in time, which second image data provision is indicated with a second entering arrow 22. Between the first point in time and the second point in time, a vascular treatment is provided to be applied to the vascular structure. The processing unit 12 is configured to combine the first and the at least one second image data 20, 22 to generate a joint outcome visualization image data 24. The display unit 16 is configured to display the joint outcome visualization image data 24.

The processing unit 12 may be configured to register the first and the second image data for the combination.

For example, for a determination of the region of interest, a spatial localization of a stenosis may be determined by detecting the stenosis in contrast-injected angiographic images, by determining pre-set markers, or by manually determining the stenosis.

Figure 2:
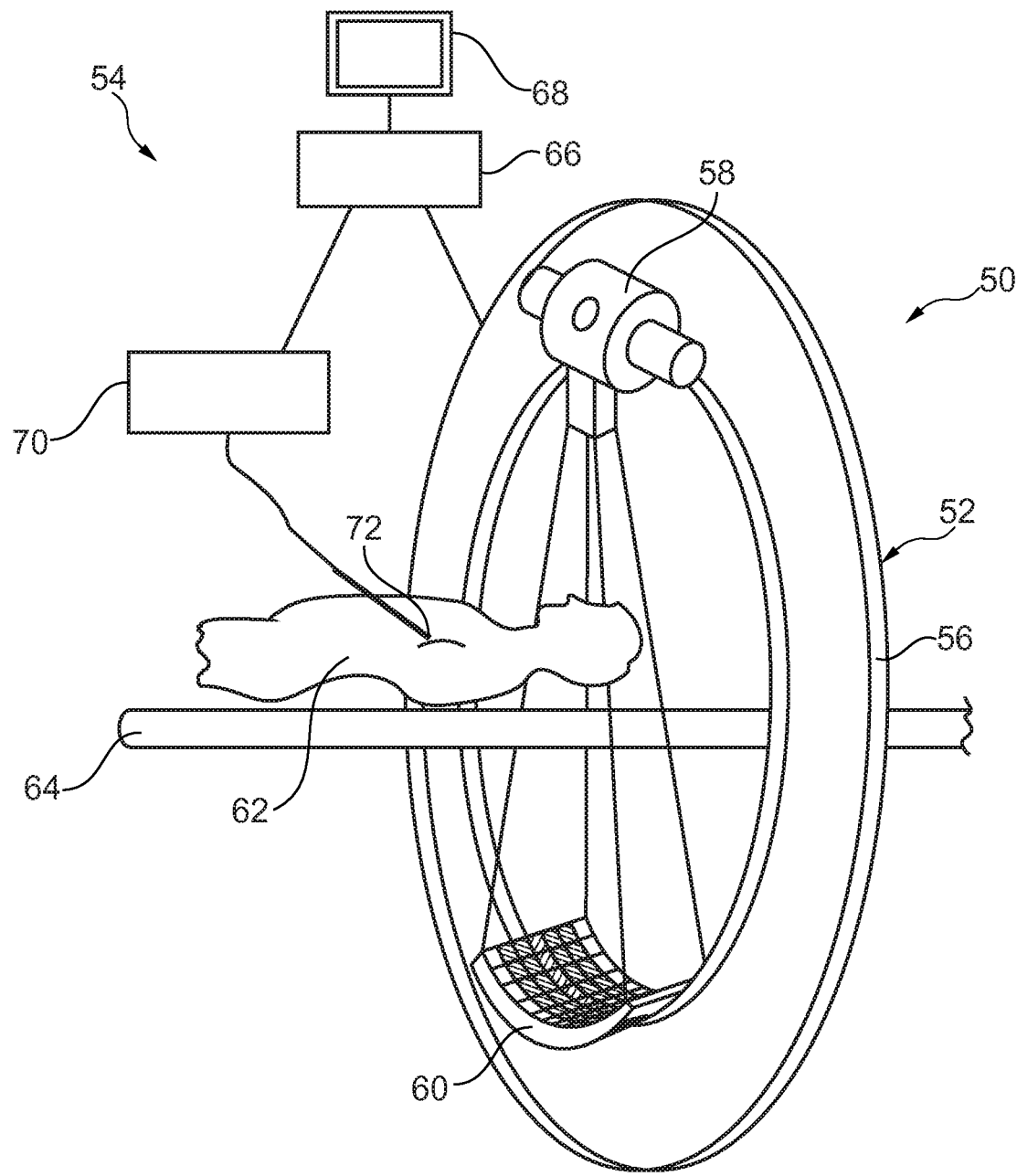
FIG. 2 schematically shows a medical imaging system for vascular treatment outcome visualization according to an exemplary embodiment of the invention.

With reference to FIG. 2, a medical imaging system 50 for vascular treatment outcome visualization is provided, comprising an image acquisition unit 52, and a device 54 for vascular treatment outcome visualization according to the above mentioned device 10 described in FIG. 1.

For example, the image acquisition unit 52 is provided as a CT arrangement with a gantry 56 and an X-ray source 58 as well as a detector 60. The X-ray source 58 and the X-ray detector 60 are arranged on the gantry such that they can be rotated around an object, for example a patient 62. A support 64, for example a table, is provided to support the object, for example a patient, during the procedure. The device 54 for vascular treatment outcome visualization is shown comprising a processing unit 66, a display unit 68, and a user control interface unit 70. The interface unit indicated with reference numeral 14 in FIG. 1 is not further shown in FIG. 2.

The image acquisition unit 52 is configured to provide the first image data of the region of interest of the vascular structure and the second image data of the region of interest of the vascular structure.

Further, an interventional device 72 is schematically indicated, which interventional device is provided to apply the vascular treatment. The interventional device 72 is configured such that it can be controlled and activated by the user interface control unit 70.

Before referring to FIG. 3 et seq., describing aspects in relation with exemplary embodiment of methods for vascular treatment outcome visualization according to the present invention, some further aspects in relation with stent placement, or stenting, as an example for a vascular treatment, shall be briefly discussed in the following.

The present invention can be used by an imaging system for percutaneous coronary intervention (PCI) in catheter laboratories, for example, to treat cardiac stenosis. For example, as a basic interventional procedure for stenting, a catheter is inserted into the vascular system, starting from an access site. The catheter is then moved along the larger vessels up to the particular vascular structure, which is to be treated. For example, by applying X-ray imaging, angiographic sequences can be recorded by cathlab X-ray equipment upon injecting contrast agent. Thus, the vessels are shown when filled with contrast agent in the images. It is explicitly noted that alternatively to X-ray imaging, also other imaging modalities are applicable, for example CT or MRI, in which contrast agent can be omitted.

During the intervention, a guide wire which is flexible and usually partially or fully radio-opaque, is advanced to the vascular structure to be treated, for example to a stenosis in the coronary system, to neurovascular aneurisms, or arteriovenous malformations. The guide wire may be visualized by low dose X-ray fluoroscopy. Upon reaching the vascular structure that requires treatment, the guide wire can then serve as a rail to deliver interventional devices, for example balloons for dilation and stent delivery, detachable coils for aneurisms, clotting, or the like. The delivery and deployment of the interventional devices may also be fluoroscopy-controlled. The inadequate expansion of the stent, the improper placement of the stent, and gap or overlap between several stents must be avoided. For example, inadequately deployed stents can cause thrombosis.

The present invention generates an image showing the lumen before stenting, overlaid to the lumen after stenting (see below). Optionally, the deployed stent may be superimposed to this image. The overlay sources, for example in case of pre-post-stenting lumen overlay two sources, or in the case of pre-post lumen plus boosted stent overlay three sources, may be correctly co-registered in case of different imaging geometries. In case of exactly matching imaging geometries, and in case of not-movement of the object, a registration can be omitted. A registration step may include spatial registration, for example mainly for breathing compensation and, if applicable, for table motion compensation, but also the temporal pairing of the source images can be provided to compensate for cardiac motion, for example. For example, the pre- and post-stenting lumens to be registered are advantageously picked in the same cardiac phase.

Figure 3:
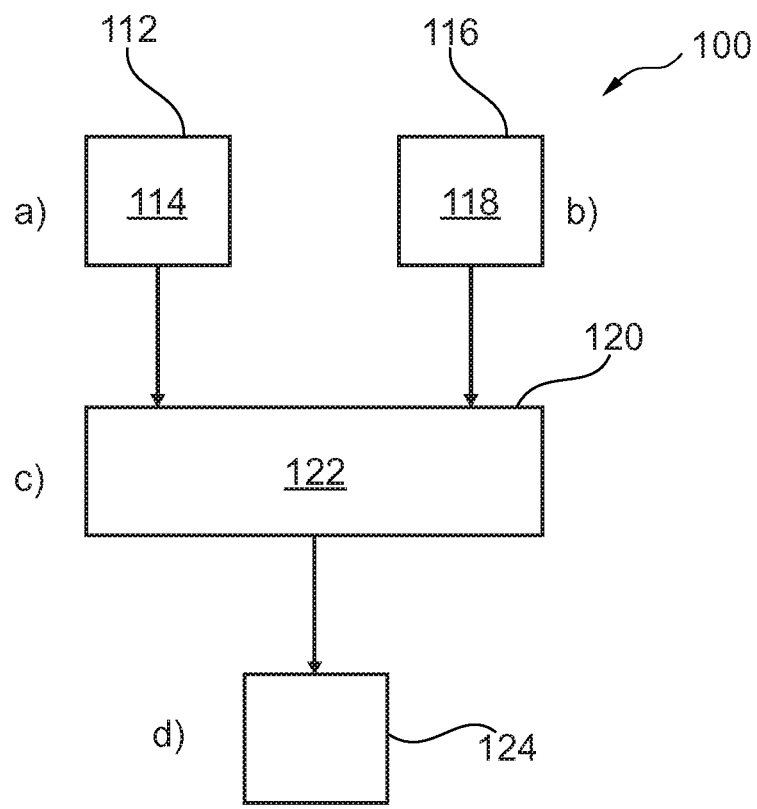
FIG. 3 schematically shows basic method steps of a method for vascular treatment outcome visualization according to an exemplary embodiment of the present invention.

As shown in FIG. 3, a method 100 for vascular treatment outcome visualization is provided. In a first provision step 112, a first image data 114 of a region of interest of a vascular structure at a first point in time is provided. In a second step provision 116, at least one second image data 118 of the region of interest of the vascular structure at a second point in time is provided. A vascular treatment is applied to the vascular structure between the first point in time and the second point in time (not further shown). In a combination step 120, the first and the at least one second image data 114, 118 are combined, generating a joint outcome visualization image data 122. In a display step 124, the joint outcome visualization image data 122 is displayed.

The first provision step 112 is also referred to as step a), the second provision step 116 as step b), the combination step 120 as step c), and the display step 124 as step d).

The first image data and the second image data may be spatially registered.

The first image data relates to the point in time, and the second image data relates to the second point in time. Following, the first image data has been acquired at a first point in time and the second image data has been acquired at a second point in time.

The first point in time relates to a pre-treatment state, and the second point in time relates to a post-treatment state. It is noted that the term "treatment" relates to the particular vascular treatments to be applied, whereas other measurements or treating steps preparing, supporting or otherwise being necessary for image acquisition in dependence of the respective imaging modality used, are not falling under the term "treatment" when used in relation to time.

For example, the vascular treatment may comprise a stenting procedure. The vascular treatment may also be another operational procedure, and the pre-treatment state refers to a pre-operational state, and the post-treatment state refers to a post-operational state.

For example, between the pre-treatment state and the post-treatment state, a medical intervention has been performed affecting the vascular structure in the region of interest.

The image data may be acquired by CT, or MRI, or X-ray, as mentioned above, with and without contrast agents.

The joint outcome visualization image may be a synthetic result evaluation image, also referred to as a synthetic result assessment image (not further shown).

Figure 4:
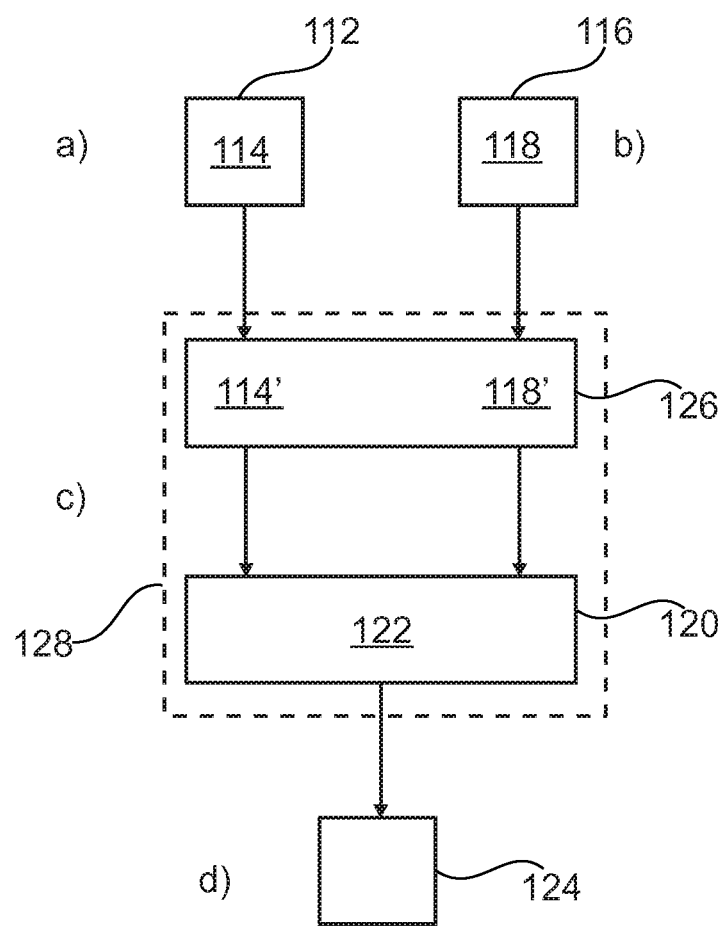
FIGS. 4 to 8 show further exemplary embodiments of a method according to the present invention.

As shown in FIG. 4, step c) may comprise a registration step 126, in which the first and the second image data 114, 118 are registered for the combination 120. The registered image data are indicated with reference numerals 114' and 118'. A common dotted frame 128 surrounds the registration step 126 and the combination 120 indicating that these two steps are related close to each other.

The registration may be based on markers provided in the region of interest, landmarks in the region of interest, vessel regions outside the treatment area but inside the region of interest and thus visible in the first and second image data, or the like.

Figure 5:
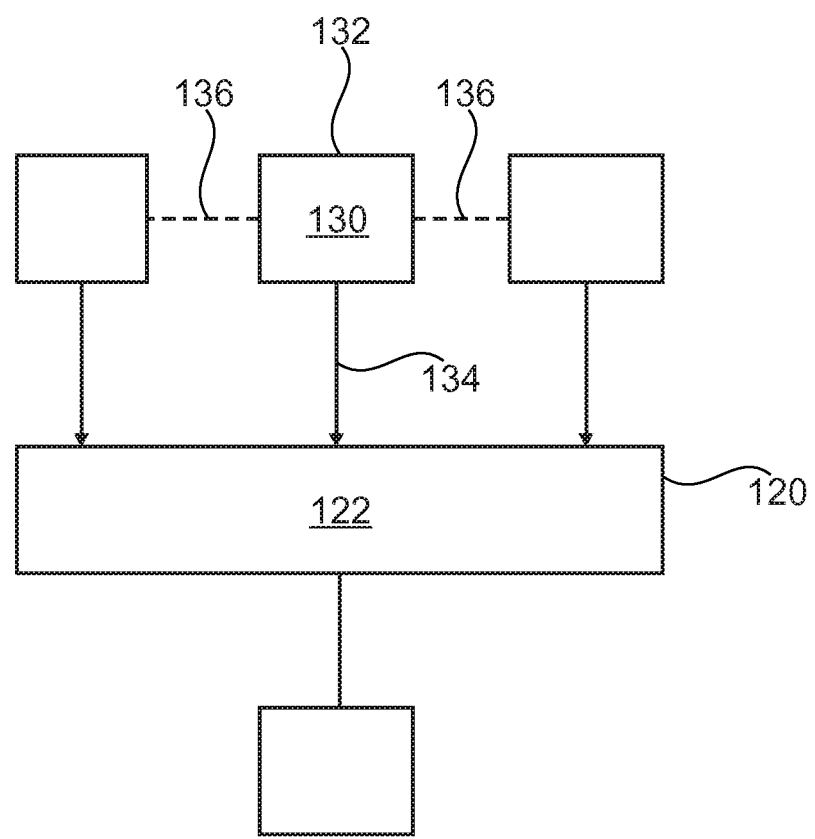
Figure 6:
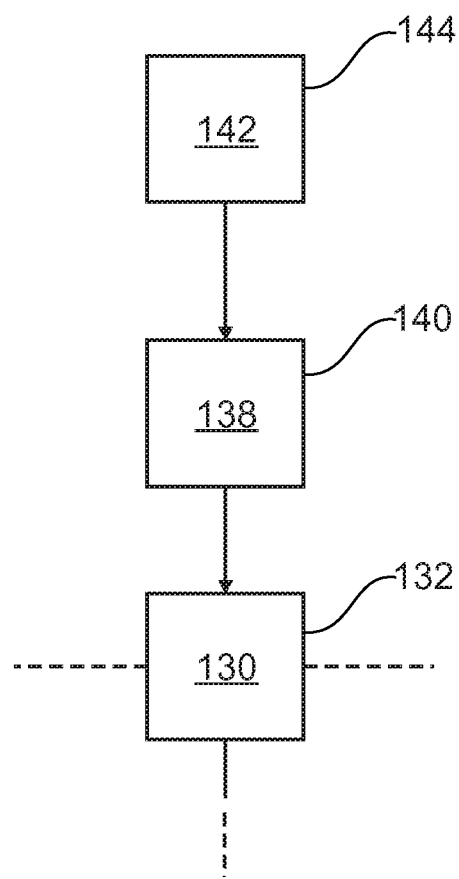

FIG. 5 relates to a further exemplary embodiment of a method, wherein the vascular treatment comprises placing a predetermined medical device inside the vascular structure (not further shown). In addition to the first image data 114 and the second image data 118, a device image data 130 is provided in a provision step 132. The device image data 130 is also combined in the combination step 120, which combination of the device image data is indicated with a further arrow 134, in order to generate the joint outcome visualization image data 122.

For the combination, the device image data 130 may be registered with at least the first or/and the second image data, which is indicated with two dotted lines 136 indicating the different options. However, it must be noted that this registration can be omitted in case of no motion appearance.

The device image data 130 provided in the provision step 132 may be an outcome 138 of at least one image processing sub-step 140, wherein the image processing sub-step 140 is based on a plurality 142 of secondary image data of the region of interest of the vascular structure after the vascular treatment being provided in a further provision step 144.

Figure 7:
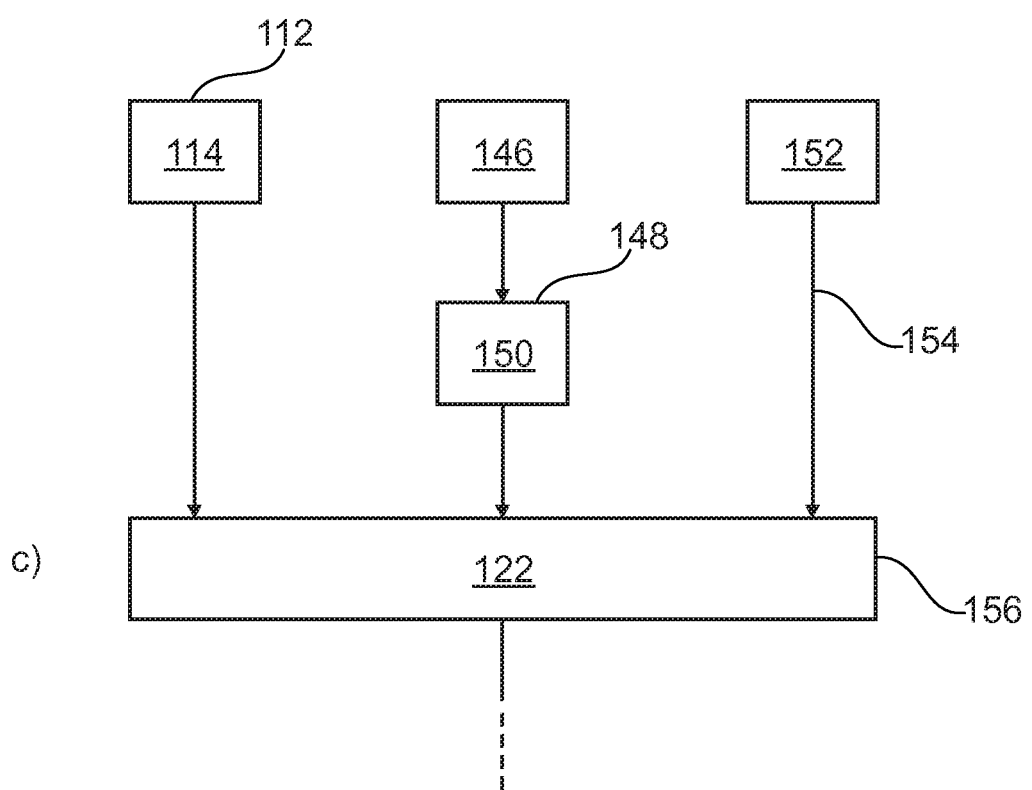

According to a further example, shown in FIG. 7, for the second image data, a plurality of images of a first subset 146 of images, in which the device is visible, are registered to each other along time in a registration sub-step 148, generating a boosted device image data 150, in which regions relating to the device are boosted. Further, at least one image of a second subset 152 of images is provided as mask image data, indicated with arrow 154, in which mask image data 154 the vascular structure is visible. The first subset of images 146 and the second subset of images 152 relate to a point in time after the vascular treatment has been applied. In step c), the first image data 114, the boosted device image data 150, and the mask image data 154 are combined in a combination step 156 to generate the joint outcome visualization image data 122. It is noted that the combination step 156 is according to the combination step 120 as described in relation with FIG. 3 et seq.

For the combination and/or registration, markers may be provided to be detectable, for example visible, in the first subset of images and in the second subset of images. This is not further shown.

Referring to the device boosting, it is noted that while the boosting of the device, the background surrounding the device is blurred in the image due to motion over time of the respective image areas or regions.

The predetermined medical device may be a stent, which is provided in a deployed state in the second point in time. In other words, the second image data is showing the actually inserted stent in the deployed state.

In step c), i.e. the combination step, the first image data 114 is superimposed, or overlaid, to the second image data 118, which also relates to superimposing or overlaying the first image data to the boosted device image data 150 and the mask image data 154.

In step c), the vascular structure of a first image data is shown in a first graphical manner, and the vascular structure of the second image data may be shown in a second graphical manner, wherein the first graphical manner is different than the second graphical manner (not further shown).

Figure 8:
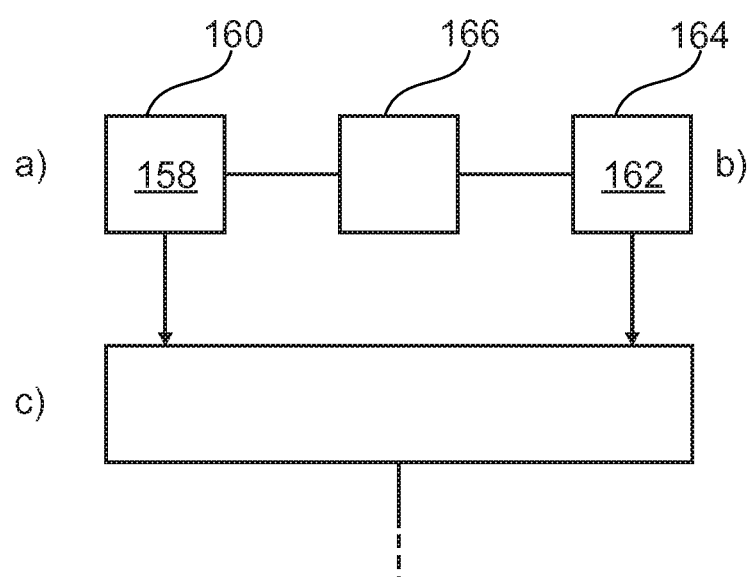

As shown in FIG. 8, in step a), a first sequence 158 of first images is provided in a provision step 160. In step b), a second sequence 162 of second images is provided in a second provision step 164. The sequences comprise several images along time. Further, the first and the second sequences 158, 162 are temporarily registered in a registration sub-step 166.

According to a further example (not further shown), a stenosis is spatially detected in the first images, for example first angiographic images, determining a first region of interest in the first angiographic images.

The first and the second images or first and second image data may be temporarily synchronized to the same cardiac phase.

For example, a second region of interest may be determined in the second angiographic images based on the first region of interest.

During the temporal registration, the first and second angiographic images may be provided with a temporal index (not further shown).

As a first image data, a first angiographic image from the first sequence of first angiographic images may be selected and, as the second image, a second angiographic image from the second sequence of second angiographic images may be selected.

For spatial matching of the first and the second image, motion compensation may be performed.

The first and the second image may be spatially synchronized to the same breathing phase.

The spatial registration may provide an aligned first region of interest and an aligned second region of interest in the respective image data.

According to a further example, although not further shown, further image data of the region of interest of the vascular structure at a further point in time is provided. The further point in time is arranged between the first and the second point in time. The further image data is also combined in step c).

For example, the second image data is superimposed on a further image data and the first image data is superimposed on the second image data being imposed on the further image data.

As mentioned or indicated above, for steps a) and b), a number of first and second images may be provided and an image or image data can be chosen according to predetermined parameters, such as best-injected image, highest contrast, etc.

Figure 9:
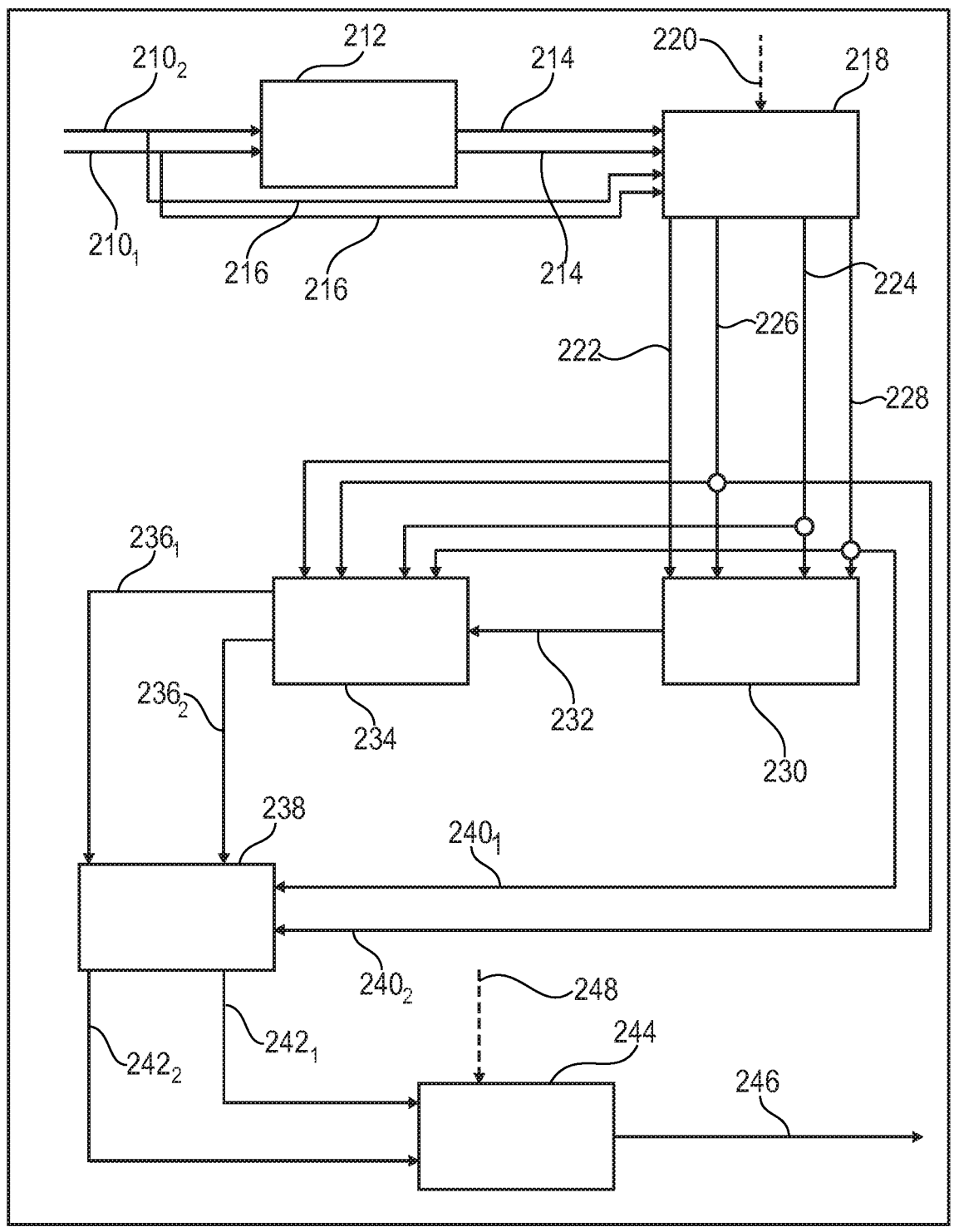
FIG. 9 shows a further exemplary embodiment of a method according to the present invention.

FIG. 9 shows a further exemplary embodiment of a method 200 according to the present invention. First arrows 210 indicate the provision of angiography-sequences. Next, a spatial detection, or spatial localization of a stenosis is provided, which is indicated with a first frame 212. The spatial localization of the stenosis may be determined in the different angiography-sequences. For example, this can be done by explicitly detecting the stenosis on the injected angiographic images, for example as vessels becoming abruptly thin; or by resorting to a stent boost strategy, where the detection is relying on the balloon markers to detect the stenosis of interest; or by manually positioning by the user.

Second arrows 214 leaving the box or frame 212 indicate the output of the spatial detection of the stenosis, i.e. the stenosis region of interest.

It is further noted that a pair of arrows is indicating that the respective pair relates to a point in time before the vascular treatment, for example before stenting, and to a second point in time after the treatment has taken place, for example after stenting. Thus, at least some of the respective reference numerals are supplemented with an index 1 relating to a state or point in time before the treatment, and with an index 2 relating to a point in time or state after the treatment. Next, by providing the stenosis region of interest, as indicated with second arrows 214, and also by providing angiography-sequences, as indicated with third arrows 216, an angiography-sequence detection step 218 is provided. For example, there may be more than two angiographies referring to the same stenosis. Also, more than one stenosis can be treated. One step therefore is to allocate the different stenosis to the corresponding angiographies (if any). When a balloon marker strategy is followed for instance, the angiographies of interest are those where the marker's position is close to the marker's location during stent boost, for example. Then, the best angiography sequences before and after stenting need to be chosen. A good choice would be to put the best-injected sequences (which can be determined automatically from the images). Of course, this could also comprise potential user interaction, as indicated with dotted arrow 220 entering the box of the angiography-sequences detection 218. As a result, or an output so-to-speak, an angiography sequence$_1$, i.e. before stenting, indicated with reference numeral 222, and an angiography sequence$_2$, i.e. after stenting, indicated with reference numeral 224, is provided. Further, a region of interest stenosis$_1$ is indicated with reference numeral 226, and a region of interest stenosis$_2$ is indicated with reference numeral 228. The four arrows 222, 224, 226, 228 enter a temporal synchronization step 230.

The goal of the temporal synchronization step 230 is to overlay the lumen before and after stenting. In order for the vessels to be comparable, they must be observed at the same cardiac phase. This step finds the temporal correspondence between the two considered angiographic sequences. This may be performed based on an ECG (not further shown), or directly on the image (for example by aligning the vessels). As a result, a temporal index correspondence 232 is provided. The above-mentioned output of the angiography-sequence detection 218 is also supplied to an instant choice step 234.

So far, the angiographic sequences are still considered. It is now necessary to identify the two images, i.e. one before and one after stenting, at the same cardiac phase, allowing the best vessel comparison. This is possible by investigation of every pair of image of the same cardiac phase and to conclude a criterion on the stenosis visibility, for example as injected as possible, and not occluded by other vessels, to pick the best couple.

The output of the instant choice step 234 is a first angiography-image 236$_1$, and a second angiography-image 236$_2$. These two angiography-images enter a spatial vessel matching step 238. Further, the spatial vessel matching 238 is also entered by the region of interest stenosis$_1$, i.e. as a result of the angiography-sequence detection 218, indicated with reference numeral 226, and the region of interest stenosis$_2$, indicated with reference numeral 228, which entering is indicated with two further arrows 240$_1$ and 240$_2$.

In the spatial vessel matching, it is taken into account that the clinician may have moved the table between the two considered exams, i.e. pre- and post-stenting, and the selected images can be in two different breathing phases, for example. Therefore, a spatial warping must be performed to enforce a perfect alignment of the portion of vessels of interest. This is possible by relying on the balloon markers. Alternatively, as an example, it is possible to filter the vessels and enforce their optimal alignment by performing a motion compensation method (block matching, daemons, etc.). It could also be possible to combine both approaches, i.e. balloon and then image, to achieve a beneficial result.

As an output of the spatial vessel matching 238, an aligned region of interest 1, indicated with reference numeral 242$_1$, i.e. pre-stenting, and an aligned region of interest 2, indicated with reference numeral 242$_2$, i.e. post-stenting, are provided to an overlay computation step 244.

In the overlay computation step 244, the output image is generated. For example, both aligned images may be colour-coded. Some image processing may be performed to enhance the vessels and/or clean the background and generate a clear output image as possible. As a result of the overlay computation 244, a final arrow 246 indicates a synthetic summary image.

It is also possible to add the stent geometry, for example as computed during stent boost, to the final image, which is indicated by a second dotted arrow 248 entering the overlay computation step 244, which second dotted arrow indicates the potential stent boost result consideration. Therefore, the balloon markers may be aligned with the post-stenting final balloon markers' position.

It is noted that the different steps detailed above have been separated for the sake of clarity. An algorithm performance will benefit from having certain steps performed together, for instance, spatial vessel matching 238 and the instant choice 234.

Figure 10:
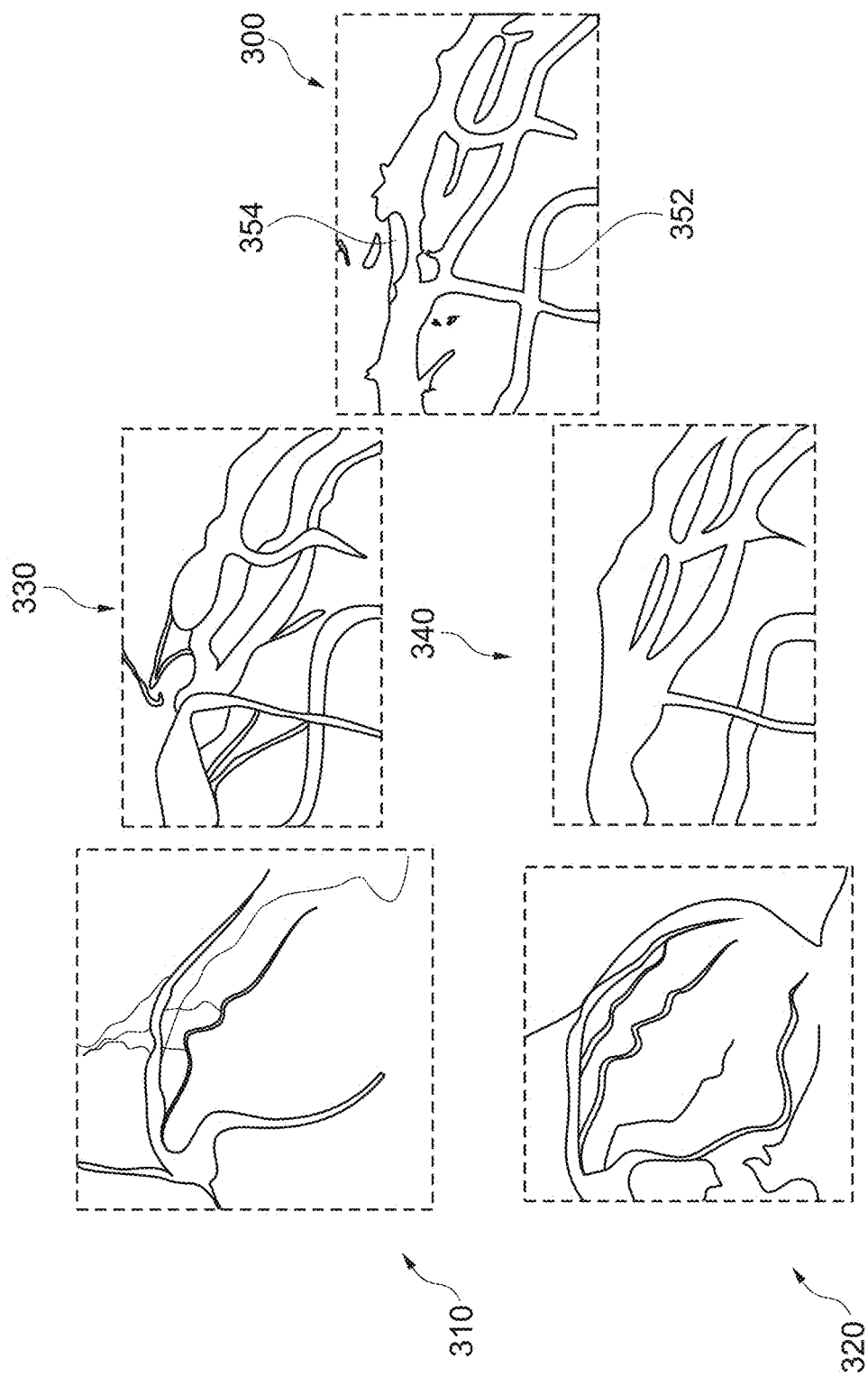
FIG. 10 shows an exemplary embodiment for a result in form of a joint outcome visualization image according to the present invention.

FIG. 10 shows an example for a joint outcome visualization image 300 in the right part. On the left column, original images are shown indicating a vessel structure before the vascular treatment in an upper image 310 and the same vessel structure after vascular treatment in a lower image 320. The centre column shows a considered stenosis region of interest, where the background has been erased, for the first state in a first enhanced image 320 in the upper row and a second image 340 for the similar considered stenosis region of interest at the second point in time in the row below.

The right side, as indicated above, shows the final result, where, for example, the original vessels are displayed in a first graphical pattern 352 and the reopened region is indicated with a second graphical pattern 354.

Figure 11:
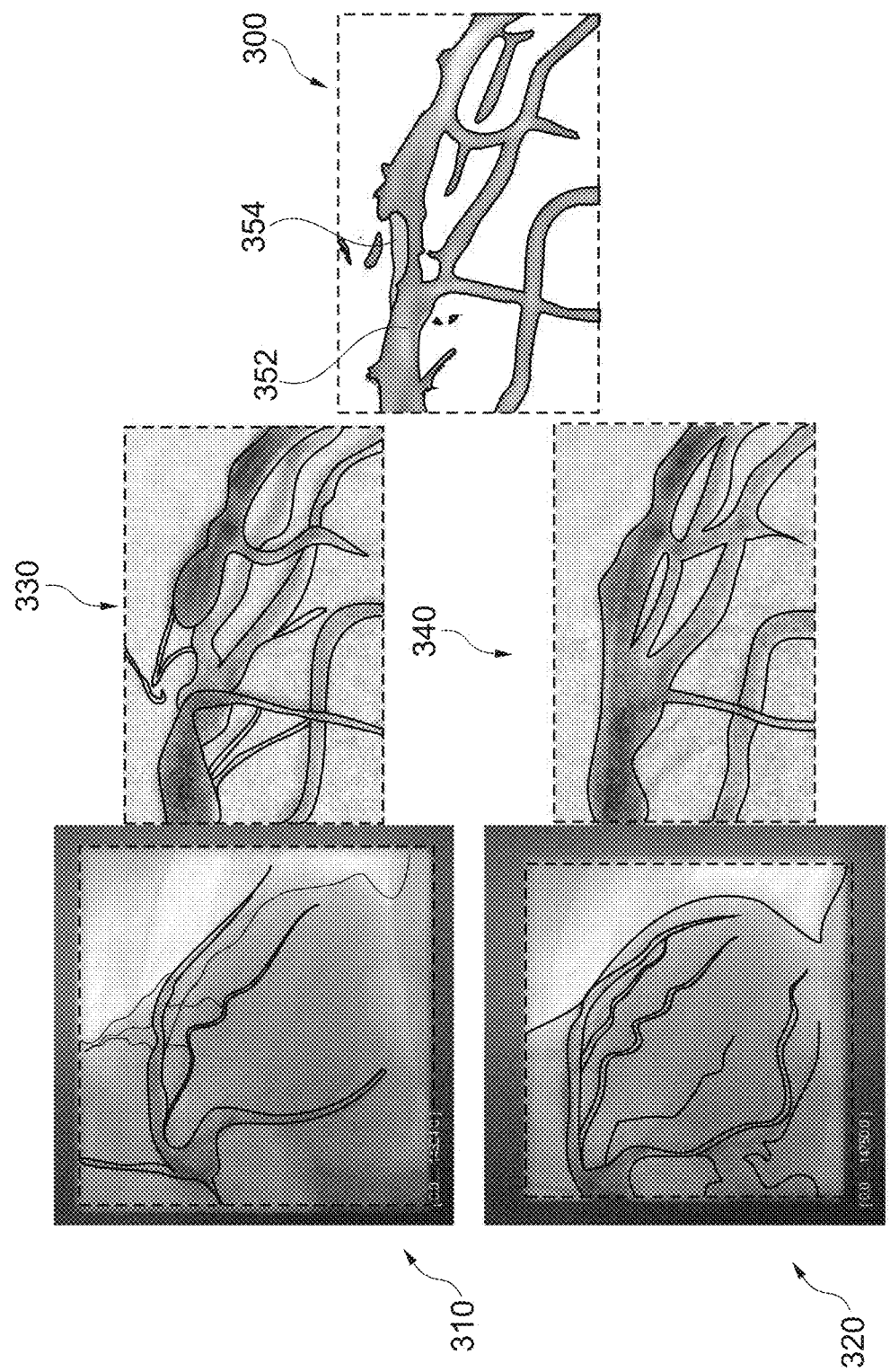
FIG. 11 shows the line drawing of FIG. 10 in relation with an X-ray image.

FIG. 11 shows the line drawing of FIG. 10 together with a photographic image of an X-ray image.

It is further noted that the output image, i.e. the joint outcome visualization image may also display more than two time instants of an intervention. If several stents are deployed in the same region, the progress of the procedure can be presented in different colours, or different graphical patterns, one for each step. It is further noted that the output does not have to be limited to one static image only, in particular, a series of images, as indicated above, one for each cardiac phase, can be generated. They can be gathered in a video (not further shown), which displays the difference between pre- and post-lumen at each cardiac phase. The variation of the method can be used to illustrate the progress of a chronic total occlusion (CTO) treatment. The application may benefit from colour-coded presentation of more than one stage of the procedure.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter, also any combination between features relating to different subject matters is considered as being disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A device for vascular treatment outcome visualization, comprising;
    an interface unit configured to provide first image data of a region of interest of an internal vascular structure at a first point in time; and to provide second image data of the region of interest at a second point in time; wherein, between the first point in time and the second point in time, a vascular treatment is applied to the internal vascular structure; wherein the first point in time relates to a pre-treatment state and the second point in time relates to a post-treatment state; and wherein, between the pre-treatment state and the post-treatment state, a medical intervention has been performed affecting the internal vascular structure in the region of interest;
    a processing unit configured to:
    receive, from the interface unit, the first image data and the second image data, wherein the first image data comprises a first sequence of first images of the pre-treatment state for each cardiac phase and the second image data comprises a second sequence of second images of the post-treatment state for each cardiac phase;
    synchronize the first sequence to temporally correspond to the second sequence based on cardiac phase, resulting in temporal pairings that each include a first image of the first sequence and a temporally corresponding second image of the second sequence;
    based on a predetermined image visibility parameter, select a temporal pairing from among the temporal pairings;
    align the selected temporal pairing by spatially matching a portion of the internal vascular structure in the first image and the second image of the selected temporal pairing; and
    combine the first image and the second image to generate a joint outcome visualization image by at least one of superimposing or overlaying the first image to the aligned second image-so as to show a lumen in the first image overlaid over the lumen in the second image; and
    a display unit configured to display the joint outcome visualization image.

2. The device according to claim 1, wherein the processing unit is configured to synchronize the first image sequence and the second image sequence for combining, by aligning at least one location in the first image data with at least one location in the second image data.

3. The device according to claim 1, wherein the vascular treatment comprises placing a predetermined medical device inside the internal vascular structure;
    wherein the interface unit is configured to provide device image data of the predetermined medical device; and
    wherein the processing unit is configured to combine the device image data, in addition to the first image and the second image, to generate the joint outcome visualisation image by at least one of superimposing or overlaying the device image data to the second image.

4. The device according to claim 3, wherein the processing unit is configured to register the device image data with at least one of the first image and the second image for combining, by aligning at least one location in the device image with at least one location in the second image.

5. The device according to claim 3, wherein the processing unit is configured to provide the device image data as an outcome of image processing based on a plurality of secondary image data of the region of interest after the vascular treatment.

6. The device according to claim 3, wherein for the second image:
    the interface unit is configured to provide a plurality of images of a first subset of images, in which the device is visible; and to provide at least one image of a second subset of images as a mask image data, in which the internal vascular structure is visible; wherein the first subset of images and the second subset of images relate to a point in time after the vascular treatment has been applied; and
    the processing unit is configured to register and combine the plurality of images of the first subset of images to each other along time to generate boosted device image data in which regions relating to the device are boosted, by aligning at least one location in each of the first subset of images; and
    wherein the processing unit is configured to combine the first image data, the boosted device image data and the mask image data, to generate the joint outcome visualization image by at least one of superimposing or overlaying the first image, the boosted device image data, and the mask image data to the second image.

7. The device according to claim 1, wherein the interface unit is configured to provide the first sequence of first images; and to provide the second sequence of second images; wherein the first sequence and the second sequence each comprise several images along time; and
    wherein the processing unit is configured to temporally synchronize the first sequence and the second sequence, by aligning at least one location in the first sequence and the second sequence.

8. The device according to claim 1, wherein the interface unit is configured to provide additional image data of the region of interest at a further point in time; wherein the further point in time is arranged between the first point in time and the second point in time; and
    wherein the processing unit is configured to also combine the additional image data, by at least one of superimposing or overlaying the additional image data to the second image to generate the joint outcome visualization image.

9. A medical imaging system for vascular treatment outcome visualization, comprising:
    an image acquisition unit; and
    a device for vascular treatment outcome visualization according to claim 1;
    wherein the image acquisition unit is configured to provide the first image data of the region of interest; and to provide the second image data of the region of interest.

10. A method for vascular treatment outcome visualization, the method comprising:
  providing, by an interface of a device, first image data of a region of interest of an internal vascular structure at a first point in time;
  providing, by the interface of the device, second image data of the region of interest at a second point in time; wherein, between the first point in time and the second point in time, a vascular treatment is applied to the internal vascular structure; wherein the first point in time relates to a pre-treatment state and the second point in time relates to a post-treatment state; and wherein, between the pre-treatment state and the post-treatment state, a medical intervention has been performed affecting the internal vascular structure in the region of interest;
  receiving, by a processor of the device from the interface of the device, the first image data and the second image data, wherein, the first image data comprises a first sequence of first images of the pre-treatment state for each cardiac phase and the second image data comprises a second sequence of second images of the post-treatment state for each cardiac phase;
  synchronizing the first sequence to temporally correspond to the second sequence based on cardiac phase, resulting in temporal pairings that each include a first image of the first sequence and a temporally corresponding second image of the second sequence;
  based on a predetermined image visibility parameter, selecting temporal pairing from among the temporal pairings;
  aligning the selected temporal pairing by spatially matching a portion of the internal vascular structure in the first image and the second image of the selected temporal pairing;
  combining, by the processor of the device, the first image and the second image to generate a joint outcome visualization image data by at least one of superimposing or overlaying the first image data to the aligned second image data so as to show a lumen in the first image overlaid over the lumen in the second image; and
  displaying, by a display of the device, the joint outcome visualization image.

11. The method according to claim 10, wherein the vascular treatment comprises placing a predetermined medical device inside the internal vascular structure;
  wherein, in addition to the first image data and the second image data, device image data of the predetermined medical device is also combined to generate the joint outcome visualization image by at least one of superimposing or overlaying the device image to the second image.

12. The method according to claim 11, further comprising:
  registering, for the second image data, a plurality of images of a first subset of images, in which the predetermined medical device is visible, to each other along time to generate boosted device image data in which regions relating to the device are boosted, by aligning at least one location in each of the plurality of images of the first subset of images; and
  providing at least one image of a second subset of images as mask image data, in which the internal vascular structure is visible; wherein the first subset of images and the second subset of images relate to a point in time after the vascular treatment has been applied,
  wherein in the combining, the first image data, the boosted device image data and the mask image data are combined, to generate the joint outcome visualization image by at least one of superimposing or overlaying the first image, the boosted device image data, and the mask image data to the second image.

13. The method according to claim 10, further comprising:
  providing additional image data of the region of interest at a further point in time is provided;
  wherein the further point in time is arranged between the first point in time and the second point in time; and
  wherein in the combining, the additional image data is also combined, to generate the joint outcome visualization image by at least one of superimposing or overlaying the additional image data to the second image.

14. A non-transitory computer readable medium that stores instructions, executable by a processor of a device for vascular treatment outcome visualization,
  wherein, when executed by the device, the instructions cause the device to perform a process for vascular treatment outcome visualization comprising:
  providing, by an interface of a device, first image data of a region of interest of an internal vascular structure at a first point in time;
  providing, by the interface of the device, second image data of the region of interest at a second point in time; wherein, between the first point in time and the second point in time, a vascular treatment is applied to the internal vascular structure; wherein the first point in time relates to a pre-treatment state and the second point in time relates to a post-treatment state;
  and wherein, between the pre-treatment state and the post treatment state, a medical intervention has been performed affecting the internal vascular structure in the region of interest;
  receiving, by a processor of the device from the interface of the device, the first image data and the second image data, wherein, the first image data comprises a first sequence of first images of the pre-treatment state for each cardiac phase and the second image data comprises a second sequence of second images of the post-treatment state for each cardiac phase;
  synchronizing the first sequence to temporally correspond to the second sequence based on cardiac phase, resulting in temporal pairings that each include a first image of the first sequence and a temporally corresponding second image of the second sequence;
  based on a predetermined image visibility parameter, selecting temporal pairing from among the temporal pairings;
  aligning the selected temporal pairing by spatially matching a portion of the internal vascular structure in the first image and the second image of the selected temporal pairing;
  combining, by the processor of the device, the first image and the second image, to generate a joint outcome visualization image by at least one of superimposing or overlaying the first image data to the aligned second image data so as to show a lumen in the first image overlaid over the lumen in the second image; and
  displaying, by a display of the device, the joint outcome visualization image.

15. The non-transitory computer readable medium of claim 14, wherein the vascular treatment comprises placing a predetermined medical device inside the internal vascular structure;

wherein the process also includes providing device image data of the predetermined medical device, and combining the device image data, in addition to the first image data and the second image data, to generate the joint outcome visualization image by at least one of superimposing or overlaying the device image data to the second image.

16. The non-transitory computer readable medium of claim 15, wherein for the second image data:

a plurality of images of a first subset of images, in which the predetermined medical device is visible, are registered to each other along time to generate boosted device image data in which regions relating to the predetermined medical device are boosted, by aligning at least one location in each of the first subset of images; and at least one image of a second subset of images is provided as a mask image data, in which the internal vascular structure is visible; wherein the first subset of images and the second subset of images relate to a point in time after the vascular treatment has been applied; and wherein in the combining, the first image data, the boosted device image data and the mask image data are combined, to generate the joint outcome visualization image by at least one of superimposing or overlaying the first image, the boosted device image data, and the mask image data to the second image.

17. The non-transitory computer readable medium of claim 15, wherein the process further includes providing additional image data of the region of interest at a further point in time;

wherein the further point in time is arranged between the first point in time and the second point in time; and wherein, in the combining, the additional image data is also at least one of superimposed or overlaid to the second image, to generate the joint outcome visualization image by at least one of superimposing or overlaying the additional image data to the second image.

18. The device according to claim 1, wherein the predetermined image visibility parameter is used to select the temporal pairing that is one of: most injected with agent or highest contrast.

19. The method according to claim 10, wherein the predetermined image visibility parameter is used to select the temporal pairing that is one of: most injected with agent or highest contrast.

20. The non-transitory computer readable medium of claim 14, wherein the predetermined image visibility parameter is used to select the temporal pairing that is one of: most injected with agent or highest contrast.

* * * * *